(12) United States Patent
Mayer et al.

(10) Patent No.: US 9,134,213 B2
(45) Date of Patent: Sep. 15, 2015

(54) METHODS FOR TESTING STRUCTURES, AND SELECTION METHODS USING THESE

(75) Inventors: John R. Mayer, The Woodlands, TX (US); Sasanka Raha, Pune (IN); Balu S. Uphade, Pune (IN); Lester K. Cantu, West Columbia, TX (US); Remi A. Trottier, Angleton, TX (US); Hwaili Soo, Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/114,204

(22) PCT Filed: May 10, 2012

(86) PCT No.: PCT/US2012/037318
§ 371 (c)(1),
(2), (4) Date: Oct. 26, 2013

(87) PCT Pub. No.: WO2012/166314
PCT Pub. Date: Dec. 6, 2012

(65) Prior Publication Data
US 2014/0090447 A1    Apr. 3, 2014

Related U.S. Application Data

(60) Provisional application No. 61/491,255, filed on May 30, 2011.

(51) Int. Cl.
*G01N 3/30* (2006.01)
*G01N 3/303* (2006.01)
*B01J 19/00* (2006.01)

(52) U.S. Cl.
CPC ............ *G01N 3/303* (2013.01); *B01J 19/0093* (2013.01); *G01N 2203/0676* (2013.01)

(58) Field of Classification Search
CPC .... C07D 301/03; B01J 23/63; B01J 19/0093; G01N 3/303; G01N 2203/0676
USPC ............... 73/12.06, 12.13; 502/208, 218
See application file for complete search history.

(56) References Cited

U.S. PATENT DOCUMENTS

| | | | |
|---|---|---|---|
| 5,051,395 A | 9/1991 | Mitchell et al. | |
| 5,057,481 A | 10/1991 | Bhasin | |
| 5,458,091 A * | 10/1995 | Pattengill et al. | 119/173 |
| 6,093,468 A * | 7/2000 | Toms et al. | 428/67 |
| 6,573,105 B1 * | 6/2003 | Kanazawa et al. | 436/155 |

OTHER PUBLICATIONS

Wu et al., "Effect of the Mechanical Failure of Catalyst Pellets on the Pressure Drop of a Reactor," Chemical Engineering Science, 2003, pp. 3995-4004, vol. 58.
Wu et al., "Mechanical Strength of Solid Catalysts: Recent Developments and Future Prospects," AIChE Journal, Oct. 2007, pp. 2618-2629, vol. 53, No. 10.

(Continued)

*Primary Examiner* — Max Noori
(74) *Attorney, Agent, or Firm* — Edward L. Brant; KSJLaw, LLC

(57) ABSTRACT

Test method for structures, e.g., such as carriers and/or catalysts. The methods may be used to select the carriers and/or catalysts for future use. Carriers and catalysts so selected, and processes making use of these, are also provided.

15 Claims, 4 Drawing Sheets

(56) References Cited

OTHER PUBLICATIONS

Germani et al., "Preparation and characterization of porous alumina-based catalyst coatings in nnicrochannels," Chemical Engineering Science, Aug. 21, 2007, pp. 5084-5091, vol. 62, No. 18-20, Oxford, GB.

R. Zapf et al., "Basic Study of Adhesion of Several Alumina-Based Washcoats Deposited on Stainless Steel Microchannels," Chemical Engineering & Technology, Dec. 1, 2006, pp. 1509-1512, vol. 29, No. 12.

* cited by examiner

METHODS FOR TESTING STRUCTURES, AND SELECTION METHODS USING THESE

FIELD

The invention relates generally to test methods for structures. The test methods may further be used in methods for the selection of structures for future use, e.g., as carriers or catalysts. The selected structures are expected to provide improved properties to the processes in which they are subsequently used.

BACKGROUND

Catalysts are important components of many chemical manufacturing processes, and may typically be used to accelerate the rate of the reaction in question and/or to increase the selectivity or efficiency towards the desired product(s). Utilized in connection with many reactions, catalysts find particular advantageous use in the epoxidation of olefins, and even more particularly in the epoxidation of alkylenes, a process of significant commercial importance in the commodity chemical business. In such epoxidation reactions, a feed containing at least the olefin/alkylene and oxygen is contacted with a catalyst causing the formation of the corresponding olefin oxide. Typically, catalysts used in alkylene epoxidation comprise a catalytic species deposited on a suitable support/carrier alone or in combination with one or more promoters.

Those of skill in the art have actively sought improvements in the selectivity and useful life of epoxidation catalysts for some time, since even incremental decreases in selectivity can be commercially detrimental. Further, catalyst failure and the changeout that it requires represent a substantial cost in epoxidation processes.

Research in this area has been wide ranging, and improvements that may provide the catalysts with increased efficiency and/or an extended useful life have been sought in the areas of components of the catalyst, e.g., carriers, promoters, and catalytic species, methods of making the catalyst and even the epoxidation processes themselves. However, it is often the case that adjustments in one or more of these may result in an improvement in one of catalyst efficiency, activity, or lifetime while yet resulting in a concurrent decrement in another. Or, any such adjustments may require conditions that cannot be produced within the epoxidation process, or if reproducible therewithin, require a reduction, or complete shut-down, in the production of the epoxidation product. Finally, once a decrease in catalyst selectivity has been detected, it can be difficult to enhance the selectivity of the catalyst or increase the catalyst lifetime by an appreciable amount, or in a commercially reasonable fashion, while yet maintaining the desired manufacturing output.

Desirably, methods would be provided that could be utilized to select catalysts, or carriers upon which the catalysts are to be based, that will exhibit a more desirable selectivity and or catalyst lifetime once in use, prior to their use. In this way, costly disruptions to manufacturing can be avoided.

BRIEF DESCRIPTION

The present invention provides such methods. More particularly, there are provided herein methods for testing structures, and methods of selection of the same based upon these test methods. The test methods involve an improved drop test wherein the results are analyzed via weight percent rather than by number percent. It has now been surprisingly discovered that structures selected based upon the results of the tests, or certain comparisons of at least two repetitions of such tests, can exhibit more desirable pressure drop characteristics when used in a catalyst bed. That is, the present test methods can be used to identify and select structures that are expected to exhibit a minimized increase in bed resistance in the first year of operation. In some embodiments, the selected structures may be used as carriers to provide the bases for catalysts, or the selected structures may be catalysts that are selected for use in a chemical process using the methods. When so used, the catalysts are expected to be capable of providing an increase in bed resistance to gas flow of up to 15%, or from 15% to 25%, during the first year of operation. The tests and selection methods based upon the same thus desirably provide a way of predicting the selectivity and/or lifetime of a catalyst bed prior to its introduction and/or use. In this way, costly disruptions to manufacturing can be avoided.

In a first aspect, there is provided a method for testing structures comprising conducting at least one repetition. Each repetition comprises causing a plurality of intact structures having a total weight to contact a surface. The weight percent of the nonintact structures generated by contact with the surface and/or other structures relative to the total weight of the plurality of intact structures is then determined. The structures may either comprise carriers or catalysts. In some embodiments, multiple repetitions may be conducted and the results compared to provide further predictors of the suitability of the structures for future use. In embodiments wherein multiple repetitions are conducted, they may be conducted with a new sample of the same, or different structures based on the originally tested sample, and at the same, or different distances from the contact surface. The method may be used to select carriers or catalysts for future use.

And so, in another aspect, there is provided a method for the production of an alkylene oxide. The method comprises selecting a type or batch of catalysts by causing a plurality of intact catalysts of that type or batch having a total weight to contact a surface. The weight percent of the nonintact catalysts generated by contact with the surface and/or other structures relative to the total weight of the plurality of intact catalysts is then determined. An alkylene and oxygen are contacted in the presence of the selected type or batch of catalysts to generate alkylene oxide.

In a further aspect, structures exhibiting a weight percent drop test result of less than 5, or 3 weight percent, or even 1.5 weight percent are provided. The structures may be either carriers or catalysts.

DESCRIPTION OF THE DRAWINGS

These and other features, aspects and advantages of the present invention may be further understood and/or illustrated when the following detailed description is considered along with the attached drawings.

DETAILED DESCRIPTION

Figure 1A:
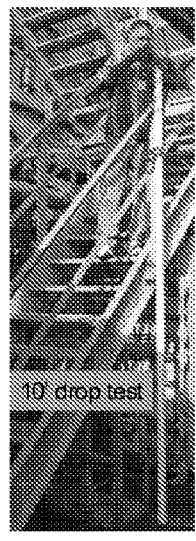
FIG. 1A is a photograph showing the setup of the present method according to one embodiment.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 25 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

One parameter that can indicate that an increase in energy usage, or a decrease in selectivity, or even catalyst failure, is forthcoming is an increase in pressure drop across the catalyst bed, which may also be referred to as pressure drop aging. One potential cause of an increase in pressure drop, in turn, may be the build-up of small particulates or fine dust within the catalyst bed. Small particulates may flow through and deposit within the catalyst bed, thereby reducing the void fraction in the catalyst bed, and thus, the pathways through which liquids or gases desirably flow. Eventually, these pathways may become partially or fully plugged, resulting in increases in bed resistance and pressure drop, and possibly, decreased time between catalyst changeout.

Although there are many potential introduction points for particulates in any chemical process, one potential introduction point may be the catalysts themselves, either at or during catalyst changeout. During such a process, catalysts are typically physically handled in operations such as pouring, loading (i.e. falling through and packing the reactor tube), sweeping, and the like. Some catalysts may suffer breakage during the process, due to impact with other catalysts, the reactor walls, or both. The breakage may result in the generation of particulates of varying sizes from the catalysts. It is believed that particulates or fines may also be generated during operation of the catalysts by, for example, mechanical vibrations, or rapid changes in the gas or liquid flow rate through the reactor or as the catalyst ages. Changes in temperature and thermal shock could also contribute to fines generation.

Conventionally, drop tests of structures, e.g., carriers and/or catalysts, have been conducted by causing a number of structures to contact a surface and then counting the number of intact structures remaining after the contact with the surface and/or other structures. In other words, conventional drop test methods utilize a number percent relative to the original number of intact structures prior to contacting to qualify carriers and/or catalysts for use. That is, in some instances, a single structure may suffer breakage into a large number of pieces, or nonintact structures, while others may suffer breakage of only a small piece or portion from the overall structure. While both situations may yield the same reduction in the number percent of intact structures, the many pieces generated in the former situation may produce a larger effect on, for example, catalyst bed pressure drop than the smaller number of nonintact structures produced in the latter situation. In either case, the number percentage of intact structures remaining after the contact may not accurately represent the suitability of the structures for further use.

In contrast, the present method calculates the weight percent of nonintact structures generated by contact and in so doing, provides a more accurate representation of the suitability of the structures for future use. When using the present method, the number of intact structures remaining is not important, and so whether a single structure breaks into multiple pieces or only two pieces is immaterial. What is important is the weight of nonintact structures generated. So, a structure that retains, e.g., 95% of its initial volume or weight may not be rejected whether the 5% that broke off broke into hundreds of tiny fragments or just a single fragment.

The present test method comprises conducting at least one repetition comprising causing a plurality of the structures desirably tested according to the present method to contact a surface. The weight percentage of nonintact structures generated by contact with the surface and/or other structures is then determined relative to the total weight of the plurality of structures caused to contact the surface. Although clearly one structure may be tested, a plurality is believed to be more representative of conditions incurred by the structures in use, e.g., during a catalyst changeout, and so, desirably, in some embodiments, a plurality of the structures having a total weight is used. Furthermore, the plurality of structures are typically a representative sample of a larger lot of structures, so that the plurality of structures tested would not, even if selected, be used, but rather, the lot of which the plurality is a representative sample would be selected.

The benefits of measuring the nonintact structures generated by contact as a weight percent are believed to extend to any form of contact, however generated, against any type of surface, whether moving or stationary. In many embodiments, it is expedient and demonstrative of commercial conditions for the plurality of structures to be released at a distance above a stationary surface. That is, catalysts may typically be loaded by pouring the desired amount of catalysts into the reactor tube, which may typically be in a substantially vertical orientation. And so, releasing the structures at some distance over a stationary surface closely resembles the conditions that the structures will experience during such aspects of their use, and performance of the structures after such release and contact predictive of the performance of the structures during use. However, the present invention is not so limited and the structures may be forcefully expelled toward a surface that may be horizontal, angled or even perpendicular.

Furthermore, the surface may be any surface reasonably predictive of a surface the structures are likely to experience during use. The surface, for example may be an indoor floor covered with any flooring material, an outdoor ground surface whether covered or uncovered, or an artificial surface, provided in any configuration. Examples of the latter include flat plates, or cups or buckets or other such containers, fabricated of any suitable material such as metal or plastic. For example, steel plates and cups or buckets fabricated from polyvinylchloride may be used. PVC typically has a hardness in the range of Shore D from 47 to 88 or Rockwell R of between 90 and 116. See, http://www.ides.com/generics/PVC/PVC_typical_properties.htm.

In those embodiments wherein the structures are caused to contact a surface by releasing the plurality of carriers at a distance above the surface, the distance used may be any that is readily accessible. In some embodiments, the distance may desirably be one reasonably predictive of conditions that the structures may encounter in use, e.g., the height of a reactor into which the structures, once formed into catalysts, may be poured. Suitable heights can be, for example, at least 5 feet (1.52 meters), at least 10 feet (3.05 meters), at least 15 feet (4.57 meters), at least 20 feet (6.09 meters), at least 25 feet (7.62 meters), at least 30 feet (9.14 meters), etc.

The height referred to herein is the distance between the surface and the point of release of the structures. It is understood by those of ordinary skill in the art that the drop height experienced by the structures may vary during the test and the surfaces that the structures contact. That is, and depending on the amount of structures being tested and the diameter of the surface onto which they are dropped, at some point, it is possible that a portion of the structures will, in fact, fall upon other structures that have covered the surface to provide a depth of structures over the surface. The structures that fall after those that cover the surface may thus contact other structures resting on the surface rather than the surface itself, and may in fact, fall a distance less than the original distance by the depth of the structures covering it. Alternatively, it may also sometimes be the case that the intact and nonintact structures are removed from the surface prior to the release of the next structure.

After contact, the weight percent of the nonintact structures, relative to the total weight of the plurality of structures prior to contact is calculated. As used herein, the phrase "intact structure" is meant to indicate a structure that has at least 90% or at least 95%, or at least 96%, or at least 97% or at least 98%, or at least 99% or even 100% of its original volume intact upon inspection, as may be carried out visually or other testing mechanisms. For example, a visual inspection carried out on, e.g., pentaring structures, may deem any structure having an entire missing segment as nonintact, and any structure having no such entire missing segments as intact. Visual inspections may also be carried out using the naked eye and a measuring device, such as a micrometer, or via any form of microscopy in combination with a measuring device.

Or, if non-visual testing methods are to be used, "intact structures" may indicate those structures that have at least 90% or at least 95%, or at least 96%, or at least 97% or at least 98%, or at least 99% or even 100% of their original volume or weight intact upon inspection, minus the standard deviation of the measurement method utilized. Thus, for example if the structures are weighed to determine whether or not they are intact, an intact structure may be deemed to be a structure that has at least 90% (minus the relative standard deviation of the scale) of the weight of an intact structure. It follows that a "nonintact structure" is meant to indicate a structure that has greater than 1%, or greater than 2%, or greater than 3%, or greater than 4%, or greater than 5%, or greater than 10% of its original volume and/or weight missing upon non-visual testing.

The phrases "original volume" and "original weight" as used herein are meant to indicate a complete structure, whatever configuration the particular structure was intended to be. Many shapes are possible for structures suitable for use as carriers and/or catalysts, and in each instance, the original shape, volume, and weight of the structure is the baseline for evaluation of the intact or nonintact structures described herein.

The present methods are believed to be more accurate predictors of successful future use than conventional methods based upon number percents. And so, the present methods can be used to select structures for further use, e.g., as carriers upon which catalysts may be based, or as catalysts in chemical processes. In embodiments wherein the same is desired, structures may be selected that generate less than 5 weight percent, or less than 4 wt %, or less than 3 wt %, or less than 2 wt %, or even less than 1.5%, nonintact structures, relative to the total weight of the plurality of structures caused to contact the desired surface from a desired height. The selected structures, when used as carriers upon which catalysts are based, or as catalysts, may provide a minimized increase in bed resistance in the first year of operation, e.g., an increase in bed resistance to gas flow of that is no greater than 25%, or no more than 20%, or even no more than 15% during the first year of operation.

In other embodiments, more than one repetition of the present method may be carried out, and the results compared to provide an additional predictor of the suitability of the structure for future use. That is, in some embodiments, an additional plurality of structures can be caused to contact a surface and the weight percent of nonintact structures generated by the contact determined relative to the total weight of the additional plurality caused to contact the surface. The result of the additional repetition may be compared to the other repetition(s), and structures selected for future use based upon this comparison.

In such embodiments, the plurality of structures can be caused to contact the surface by the same method, e.g., releasing the pluralities from the same distance, or a different distance, above the surface. For example, both pluralities may be released from a distance 10 feet above the surface, or, one plurality may be released at a distance of 10 feet above the surface, and an additional plurality may be released at a distance of 15 feet, or 20 feet, or even 30 feet above, the surface.

And, in such embodiments, the structures may comprise carriers in one or more repetitions and catalysts in others and the results of the repetitions compared. For example, one plurality of carriers may be released at a distance of 10 feet above a surface, and a second plurality of structures comprising catalyst may be released at a distance of 10 feet, or 20 feet, or 30 feet, above the surface. The weight percent of nonintact carriers may then be compared to the weight percent of nonintact catalysts generated. In such embodiments, particularly illustrative comparisons result when the carriers of the same type or batch as tested are used as the bases of the catalysts tested so that the comparison is between the weight percent of nonintact carriers and the weight percent of nonintact catalysts prepared upon the same type or batch of carriers.

It has now been surprisingly discovered that such comparisons provide further indicators of the suitability of the carriers for use as a bases for the catalysts and/or the catalysts for use in a chemical process. For example, carriers and/or catalysts whose results in the individual repetitions do not differ substantially, or differ by no more than 3 wt %, or even by no more than 5 wt %, when used as carriers upon which catalysts are based, or as catalysts, may provide an increase in bed resistance to gas flow during one year of operation that is no greater than 25%, or no more than 20%, or even no more than 15% of the early life resistance of the structures.

As used herein, the term "structure" applies to either a carrier, or a carrier that has been impregnated with at least one catalytic species to provide a catalyst. The method described herein is expected to be useful when applied to any such carrier or catalyst, and is not particularly limited in this regard.

One class of structures that may find particular benefit from application of the present invention includes carriers and/or catalysts useful for the epoxidation of olefins, and in particular, for the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer's Encyclopedia of Chemical Technology, 4$^{th}$ Ed. (1994) Volume 9, pages 915-959. Although the invention is not so limited, for purposes of simplicity and illustration, application of the present method is further described in terms of and with reference to catalysts useful for the epoxidation of ethylene.

Generally, such carriers may comprise any of the large number of known porous refractory structure or support materials, so long as whatever the porous refractory material chosen, it is relatively inert in the presence of the chemicals and processing conditions employed in the application in which the shaped porous body will be utilized. It may also be important that the support materials, and thus catalysts based upon the same, generally be able to withstand fairly large temperature and pressure fluctuations within the reactor.

There are many well-known methods of preparing supports suitable for use in alkylene oxide catalysts. Some of such methods are described in, for example, U.S. Pat. Nos. 4,379,134; 4,806,518; 5,063,195; 5,384,302; 6,831,037 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity and/or pore size distribution after its removal during the calcination step. The levels of impurities in the finished support are determined by the purity of the raw materials used, their degree of volatilization during the calcination step or removal of impurities by treating (e.g. washing) the formed carrier post calcination step. Common impurities may include silica, alkali and alkaline earth metal oxides and trace amounts of metal and/or non-metal-containing additives.

Another method for preparing a support having particularly suitable properties for alkylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina support.

Suitable carriers may typically comprise at least 80 weight percent alpha-alumina and comprises less than 30 parts per million acid-leachable alkali metals by weight, the weight percent of the alpha-alumina and the concentration of the acid-leachable alkali metals being calculated on the weight of the support, where the acid-leachable alkali metals are selected from lithium, sodium, potassium, and mixtures thereof.

Suitable carriers may further comprise any other component, in any amounts, necessary or desired for processing, such as, e.g., water, acid, binders, lubricants dispersants, pore formers, dopants, modifiers, etc, such as those described in *Introduction to the Principles of Ceramic Processing*, J. Reed, Wiley Interscience, (1988).

The present methods may advantageously be applied to carriers that are desirably porous and have measured BET surface areas of at least 0.5 m$^2$/g (more preferably from 0.7 m$^2$/g to 10 m$^2$/g), measured pore volumes of at least 0.3 cc/g (more preferably from 0.4 cc/g to 2.0 cc/g), and median pore diameters from 1 to 50 microns.

"BET surface area", as used herein, refers to the surface area as measured by the BET (Brunauer, Emmett and Teller) method by nitrogen as described in the Journal of the American Chemical Society 60 (1938) pp. 309-316. "Total pore volume" means pore volume of the support material and is typically determined by mercury porosimetry. "Porosity" is the proportion of the non-solid volume to the total volume of material. Total pore volume as measured by mercury porosimetry or water absorption may be used to estimate porosity by those of skill in the art. "Median pore diameter" means the pore diameter corresponding to the point in the pore size distribution at which half of the total pore volume of the shaped porous body has been measured.

The carriers/catalysts can be of any desired, suitable shape. Conventional commercial fixed bed ethylene oxide reactors are typically in the form of a plurality of parallel elongated tubes (in a suitable shell) having an outer diameter of from 2 to 7 cm and a length of from 4 to 14 m. For use in such fixed bed reactors, the carriers/catalysts will desirably be formed into a rounded shape, such as, for example, spheres, pellets, rings, tablets, and the like, having diameters from 0.1 inch (0.25 cm) to 0.8 inch (2 cm).

Epoxidation catalysts, in turn, include at least one catalytic species deposited on the desired carrier. Non-limiting examples of catalytic species that may advantageously be supported by the support material include metals, solid state compounds, molecular catalysts, enzymes and combinations of these. Typically, catalysts useful for the epoxidation of ethylene utilize silver as the catalytic species, and the same can be preferred in some embodiments.

In such embodiments, any desired catalytic amount of silver, i.e., any amount of silver capable of catalyzing the direct oxidation of, e.g., ethylene, with oxygen or an oxygen-containing gas to the corresponding alkylene oxide, may be used. Typically, the support material will be impregnated with one or more silver compound solutions sufficient to allow the silver to be provided on the support material in an amount greater than 5 percent, greater than 10 percent, greater than 15 percent, greater than 20 percent, greater than 25 percent, preferably, greater than 27 percent, and more preferably, greater than 30 percent by weight, based on the weight of the catalyst. Although the amount of silver utilized is not particularly limited, the amount of silver provided in connection with the support material may usually be less than 70 percent, and more preferably, less than 50 percent by weight, based on the weight of the catalysts.

In terms of density, the catalytic species, e.g., silver, relative to the BET surface area of the support material may be present in amounts up to at least 0.07 g/m$^2$, or up to 0.2 g/m$^2$, or even up to 0.3 g/m$^2$ or more.

Although silver particle size in the finished catalysts is important, the range is not narrow. A suitable silver particle size can be in the range of from 10 angstroms to 10,000 angstroms in diameter. A preferred silver particle size ranges from greater than 100 angstroms to less than 5,000 angstroms in diameter. It is desirable that the silver be relatively uniformly dispersed within, throughout, and/or on the support material.

Catalysts according to the present invention desirably comprise rhenium, and may, in certain embodiments, further include one or more additional promoters. Rhenium promoted supported silver containing catalysts are known from U.S. Pat. Nos. 4,761,394 and 4,766,105. Broadly, the catalysts comprise silver, rhenium or compound thereof, and in some embodiments, a co-promoter such as a further metal or compound thereof and optionally an additional co-promoter such as one or more of sulfur, phosphorus, boron, and compounds thereof, on the support material. As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

Known promoters for silver based catalysts for the epoxidation of ethylene include, but are not limited to, rhenium, molybdenum, tungsten, lithium, sulfur, manganese, potassium, rubidium, and cesium. Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261.

The rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered as a source for a perrhenate, that is, $ReO_4$. Similar chemistries can be exhibited by other metals such as molybdenum and tungsten.

Catalysts comprising silver as a catalytic species as well as at least rhenium as a promoter are expected to find particular benefit from application of the present invention, and such catalysts are preferred. In some embodiments, the catalysts may also desirably comprise a promoting amount of at least one further metal, and optionally, a co-promoter. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, sodium, rubidium and cesium and/or from the Group IIA metals such as calcium and barium. Most preferably it is lithium, potassium, sodium and/or cesium. Where possible, rhenium, the further metal or the co-promoter is provided as an oxyanion, in salt or acid form. The metals, as well as the rhenium promoter may each be present in a quantity of from 0.01 to 500 mmole/kg, calculated as the element (rhenium or metal) on the total catalyst. Optional co-promoters include, but are not limited to: tungsten, manganese, molybdenum, chromium, sulfur, phosphorous, boron, and mixtures thereof.

The supported silver catalyst can comprise a rhenium promoter, a first co-promoter, and a second co-promoter; where the quantity of the rhenium promoter deposited on the carrier is greater than 1 mmole/kg, relative to the weight of the catalyst; where the first co-promoter is selected from sulfur, phosphorus, boron, and mixtures thereof; where the second co-promoter is selected from tungsten, molybdenum, chromium, and mixtures thereof; and the total quantity of the first co-promoter and the second co-promoter deposited on the carrier is at most 3.8 mmole/kg, relative to the weight of the catalyst.

The catalyst can comprise a carrier and, deposited on the carrier, silver, a rhenium promoter, a first co-promoter, and a second co-promoter; wherein the molar ratio of the first co-promoter to the second co-promoter is greater than 1, wherein the first co-promoter is selected from sulfur, phosphorus, boron, and mixtures thereof; and wherein the second co-promoter is selected from tungsten, molybdenum, chromium, and mixtures thereof. The catalyst can comprise silver, a rhenium promoter, a first co-promoter, and a second co-promoter on a carrier; wherein the molar ratio of the first co-promoter to the second co-promoter is greater than 1; wherein the first co-promoter is selected from sulfur, phosphorus, boron, and mixtures thereof; and the second co-promoter is selected from tungsten, molybdenum, chromium, and mixtures thereof.

The rhenium and any other desired promoters included in the catalyst to be subjected to the present method, are desirably provided in a promoting amount, and such amounts are readily determined by those of ordinary skill in the art. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as, for example, reaction conditions, catalyst preparative techniques, BET surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Exemplary suitable amounts of rhenium are expected to range from 0.0001 weight percent (1 ppmw) to 2 weight percent (20,000 ppmw), preferably from 0.0005 weight percent (5 ppmw) to 0.5 weight percent (5000 ppmw) based on the total weight of the catalyst. When used, the rhenium component may often be provided in an amount of at least 1 ppmw, say, at least 5 ppmw, for example, or from 10 ppmw to 2000 ppmw, often between 20 ppmw and 1000 ppmw, calculated as the weight of rhenium based on the total weight of the catalyst.

Methods of preparing epoxidation catalysts are well-known in the art, and any of these are suitable for use in preparing the catalysts to be subjected to the present methods. Generally speaking, the methods involved one or more impregnation steps with one or more solutions comprising the desired catalyst components. Typically, a reduction step is conducted during or after the impregnations, to form metallic silver particles. Thorsteinson et al., U.S. Pat. No. 5,187,140, for example, describes methods of forming catalysts.

It has now been surprisingly discovered that the weight percent drop test methods described herein can be used to predict certain aspects of catalyst behavior over its operating life even prior to loading in a reactor. Application of the present method can thus facilitate selection of catalysts that provide an increase in bed resistance to gas flow during first one year of operation that is no greater than 25%, or 20%, or even 15%, of the early life resistance. This can reduce the energy consumption and/or the effect on catalyst efficiency caused by lowered flow rates and space velocities as the catalyst ages. Selected catalysts can thus provide increased time intervals between catalyst change-out, and significant cost and time savings.

As such, the present invention also provides a method for the epoxidation of alkylenes using catalysts selected by the disclosed methods. Those of ordinary skill in the chemical engineering art are familiar with such processes. One exemplary process is described in Kirk-Othmer's Encyclopedia of Chemical Technology, 4$^{th}$ ed., Vol. 9, 1994, pp. 925-939.

Generally speaking then, the epoxidation reaction may take place in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics.

The epoxidation reaction is generally exothermic. Thus, a coolant system (e.g., a cooling jacket or a hydraulic circuit with a coolant fluid such as a heat transfer fluid or boiling water) may be provided to regulate the temperature of the reactors. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature.

Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas and a gas phase promoter at parts per million level to a catalyst-containing reactor at a temperature of from 200° C. to 300° C., and a pressure which may vary between 5 atmospheres (506 kPa) and 30 atmospheres (3.0 MPa), depending upon the mass velocity and productivity desired. Oxygen may be supplied to the reaction in an oxygen-containing stream, such as, air or as pure oxygen, or as oxygen-enriched air. The resulting alkylene oxide, preferably, ethylene oxide, is separated and recovered from the reaction products using conventional methods.

Any alkylene can be utilized in the process, and examples of those that may desirably be epoxidized include, but are not limited to, 1,9-decadiene, 1,3-butadiene, 2-butene, isobutene, 1-butene, propylene, ethylene, or combinations of these. Preferably, the alkylene comprises ethylene.

Typically, epoxidation reactions may desirably be carried out in the gas phase, with a feed comprising the desired alkylene and oxygen being caused to come in contact with the epoxidation catalyst selected according to the present method. Oftentimes, the selected catalyst is present as a packed bed within the desired reactor. The quantity of catalyst in the packed bed may be at least 10 kg, or at least 20 kg, or from $10^2$ to $10^7$ kg or from $10^3$ to $10^6$ kg.

Many epoxidation reactions are carried out as continuous processes, and the same is contemplated here. In such processes, the desired reactor may typically be equipped with heat exchange equipment to control the temperature of the process, within the reactor and/or the catalyst bed.

In one embodiment, the process for the oxidation of an alkylene comprises contacting a reaction mixture feed comprising an alkene, oxygen, and carbon dioxide, with a catalyst selected according to the present method and comprising silver, a rhenium promoter, a first co-promoter, and a second co-promoter; the first co-promoter is selected from sulfur, phosphorus, boron, and mixtures thereof; and the second co-promoter is selected from tungsten, molybdenum, chromium, and mixtures thereof.

During operation, the pressure at the inlet of the epoxidation reactor may typically be less than 4000 kPa, or less than 3500 kPa, or preferably will be less than 2500 kPa absolute, and in most instances will be at least 1000 kPa absolute. The gas hourly space velocity, ("GHSV") is the unit volume of gas at standard state temperature and pressure (0° C., 1 atm) passing over one unit volume of packed catalyst bed per hour. Preferably in those embodiments wherein the epoxidation reaction is carried out in the gas phase, over a packed catalyst bed, the GHSV in the start-up phase is desirably from 2000 to 10000 per hour.

The alkylene oxide produced by the present epoxidation process may typically be processed to provide further downstream products, such as, for example, 1,2-diols, 1,2-diol ethers, 1,2-carbonates, and alkanolamines. Since the present invention provides an improved epoxidation method, it is contemplated that the improvements provided will carry forward to provide improvements to these downstream processes and/or products. Improved methods for the production of 1,2-diols, 1,2-carbonates, 1,2-diol ethers and alkanolamines are thus also provided herein.

The conversion of alkylene oxides into 1,2-diols or 1,2-diol ethers may comprise, for example, reacting the desired alkylene oxide with water, suitably in the presence of an acidic or basic catalyst. For example, for preferential production of the 1,2-diol over the 1,2-diol ether, the alkylene oxide may be reacted with a tenfold molar excess of water, in a liquid phase reaction in the presence of an acid catalyst, e.g., 0.5-1.0 wt % sulfuric acid, based on the total reaction mixture, at 50-70 C at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternative 1,2-diol ethers may be prepared by converting the alkylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of alkylene oxides produced via the method of the present invention into alkanolamines may comprise, for example, reacting the alkylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897.

Some embodiments of the invention will now be described in detail in the following examples.

EXAMPLE 1

Figure 1B:
FIG. 1B is a photograph showing the setup of the present method according to one embodiment.
Figure 1C:
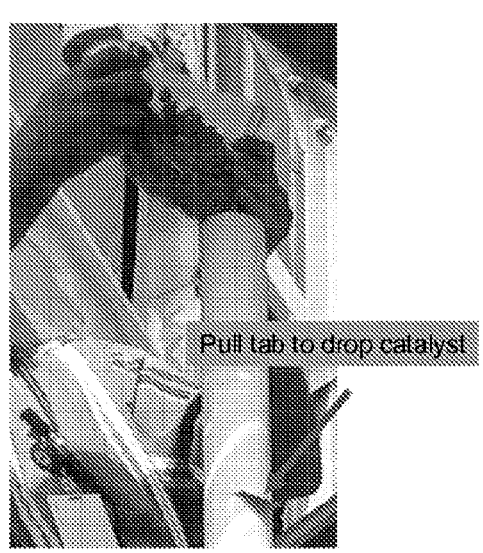
FIG. 1C is a photograph showing the setup of the present method according to one embodiment.

Three 10' sections of 2" diameter PVC pipes are assembled to provide a 10', 20', or a 30' drop as shown in FIGS. 1A and 1B (10' and 30' drop shown). A pull tab is installed at a distance of 1 foot from the top of the tube as shown in FIG. 1C. The carrier or catalyst sample is poured into the top section of the tube and retained by the pull tab (FIG. 1C). The amount of catalyst that fills the top foot segment of the tube is used. The bottom of the tube is fitted with a PVC cap to retain the sample.

The experiment is carried out with an intact carrier or catalyst sample that is hand sorted prior to the drop test so that the sample comprised 100 wt % intact carriers. The nonintact carriers are removed from the sample prior to the test. For this particular sample as received directly from the carrier manufacturer, the nonintact carriers make up 3.3% wt of the total weight of the carrier sample (prior to sorting, nonintact plus intact carriers). As a result, all nonintact carriers found in the sample after the test are generated by the impact of the individual carriers or catalysts with the surface.

Figure 2:
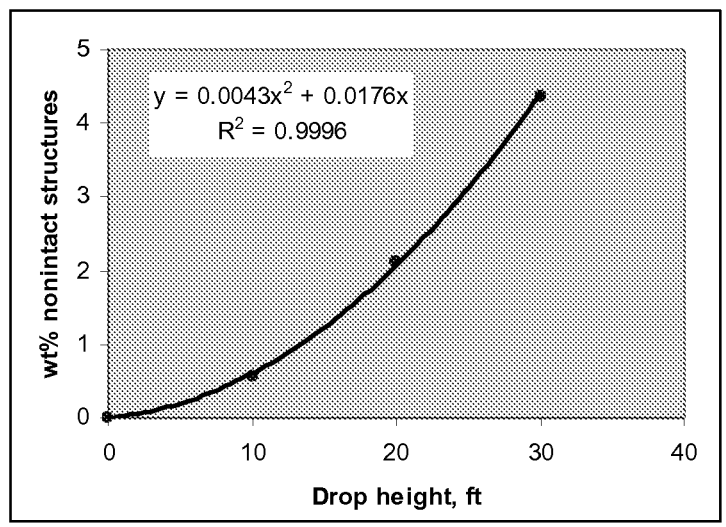
FIG. 2 is a graphical depiction of the weight percent nonintact structures generated as a function of drop height.

The drop experiment is repeated 3 times with each sample at each of three different heights—10', 20', and 30'. The resulting data from all experiments is shown in Table 1 and illustrated in FIG. 2.

Since it is expected that no breakage would occur at a drop height of zero, the point (0,0) is added as a data point on the graph. This point is also included in the calculation of the equation of the curve. For drop heights greater than 10 ft, the breakage is mostly influenced by the square term in the equation of the curve shown in FIG. 2. The weight % nonintact pieces is therefore approximately proportional to the square of the drop height. This square relationship is expected to eventually level off at heights where the pill velocity approaches terminal velocity.

TABLE 1

|  | 10 feet | | | 20 feet | | | 30 feet | | |
|---|---|---|---|---|---|---|---|---|---|
|  | \multicolumn{9}{c}{Run #} |
|  | 1 | 2 | 3 | 1 | 2 | 3 | 1 | 2 | 3 |
| Sample Wt. (gm) | 472.2 | 472.1 | 471.7 | 472 | 471.7 | 471.3 | 471.3 | 468.8 | 471.8 |
| Nonintact Wt. (gm) | 1.7 | 2.8 | 3.3 | 10.2 | 9.7 | 10 | 17.2 | 21 | 23.5 |
| Nonintact Wt. % | 0.36 | 0.59 | 0.70 | 2.16 | 2.06 | 2.12 | 3.65 | 4.48 | 4.98 |
| Avg. Wt. % |  | 0.55 |  |  | 2.11 |  |  | 4.37 |  |

EXAMPLE 2

Carriers and catalysts are tested according to some embodiments as described above in Example 1. The results are shown in FIGS. 3A and 3B, respectively.

Figure 3A:
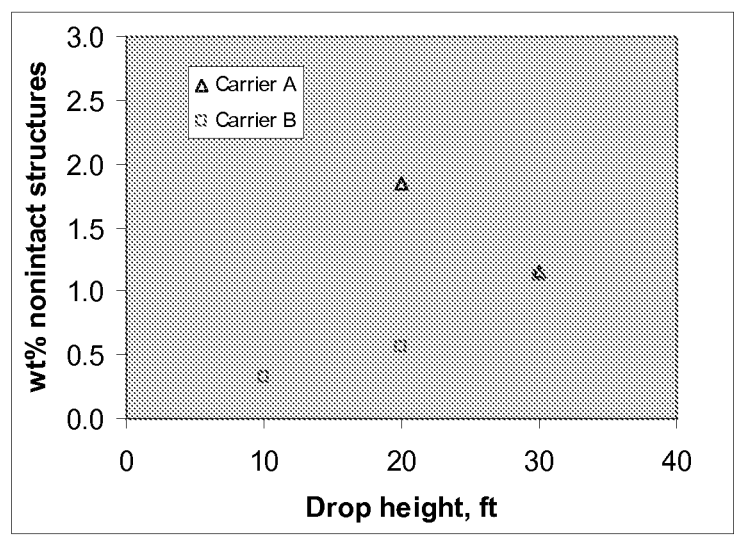
FIG. 3A is a graphical depiction of weight percent nonintact structures generated as a function of drop height.

As shown in FIG. 3A, both carrier lots A and B produce less than 3 wt % nonintact carriers when tested at heights of up to 30 feet. Furthermore, the difference in wt % nonintact carriers generated by each lot at different test heights does not vary by more than 1 wt %. Thus, both of these lots of carriers would be selected for use in the preparation of catalysts according to the present method.

Figure 3B:
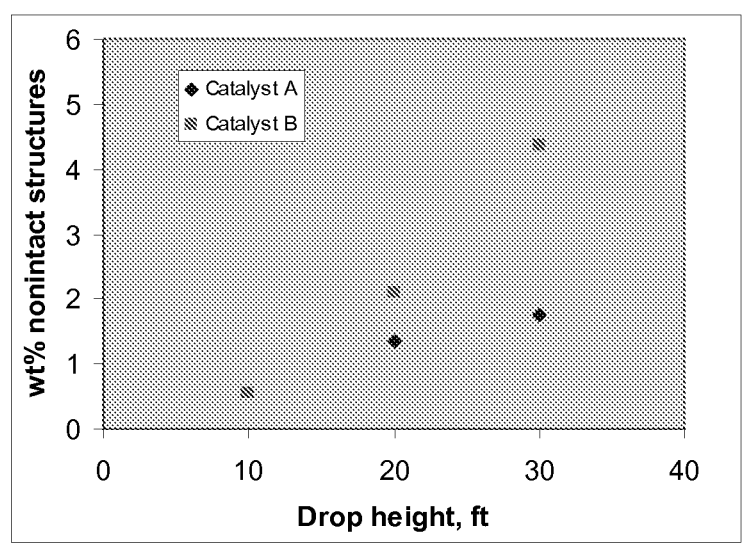
FIG. 3B is a graphical depiction of the weight percent nonintact structures generated as a function of drop height.

As shown in FIG. 3B, while catalyst lot A produces less than 3 wt % nonintact catalysts when tested at heights of up to 30 feet and a difference in wt % nonintact catalysts generated by testing at different heights that does not vary by more than 1 wt %, catalyst lot B does not. Catalyst A would thus be selected for use in a chemical process, and when so used, would be expected to result in an increase in pressure drop during first year operation of the catalyst of less than 20% of early life bed resistance. Catalyst B would not be selected for use, and if used, would be expected to exhibit an increase in pressure drop during first year of operation of the catalyst of 20% or greater of early life bed resistance.

The invention claimed is:

1. A method for testing structures for suitability for use in an epoxidation process comprising:
Conducting at least one repetition comprising:
Causing a plurality of intact structures having a total weight to contact a surface by releasing the plurality of structures at a distance above the surface;
Determining the weight percent of the nonintact structures generated by contact with the surface and/or other structures relative to the total weight of the plurality of intact structures, wherein the structures are carriers comprising at least 80 weight percent alpha-alumina and/or catalysts based upon carriers comprising at least 80 weight percent alpha-alumina.

2. The method of claim 1, further comprising selecting structures for further use for which the test method generates less than 3 wt % nonintact structures and wherein the structures comprise carriers comprising at least 80 weight percent alpha alumina and the selected carriers are used to prepare catalysts.

3. The method of claim 2, wherein the structures comprise catalysts and the selected catalysts are used in the epoxidation process.

4. The method of claim 1, comprising conducting at least two repetitions, comparing the weight percent of nonintact structures obtained in each repetition, and selecting those structures for further use for which the weight percent of the nonintact structures obtained in one repetition and the weight percent of the nonintact structures obtained in another repetition do not differ by more than 5 wt % and wherein in each repetition, the structures comprise carriers comprising at least 80 weight percent alpha alumina and the selected carriers are used to prepare catalysts.

5. The method of claim 4, wherein the selected carriers are used in the manufacture of ethylene oxide catalysts.

6. The method of claim 1, comprising conducting at least two repetitions, comparing the weight percent of nonintact structures obtained in each repetition, and selecting those structures for further use for which the weight percent of the nonintact structures obtained in one repetition and the weight percent of the nonintact structures obtained in another repetition do not differ by more than 5 wt % and wherein in each repetition, the structures comprise_catalysts and the selected catalysts are used in a chemical process.

7. The method of claim 6, wherein the selected catalysts are used in a process for the production of ethylene oxide.

8. The method of claim 1, comprising conducting at least two repetitions, comparing the weight percent of nonintact structures obtained in each repetition, and selecting those structures for further use for which the weight percent of the nonintact structures obtained in one repetition and the weight percent of the nonintact structures obtained in another repetition do not differ by more than 5 wt % and wherein in a first repetition, the structures comprise carriers comprising at least 80 weight percent alpha alumina and in a second repetition the structures comprise catalysts and the selected carriers are used to prepare catalysts, and/or the selected catalysts are used in a chemical process.

9. The method of claim 4, wherein the distance from which the structures are released differs between at least two repetitions.

10. A process for the production of an alkylene oxide comprising:
Selecting catalysts for use in the process according to the method of claim 1, wherein the structures comprise catalysts; and
Contacting an alkylene and oxygen in the presence of the selected catalysts to generate alkylene oxide.

11. A structure suitable for use in an epoxidation process that exhibits a weight percent drop test result of less than 5 weight percent, wherein the structure is a carrier comprising at least 80 weight percent alpha alumina and/or a catalyst based upon a carrier comprising at least 80 weight percent alpha alumina.

12. The structure of claim 11, comprising a carrier.

13. The structure of claim 12, wherein the carrier comprises total porosity of greater than 0.4 cc/g.

14. The structure of claim 11, comprising a catalyst.

15. The structure of claim 14, wherein the catalyst is used in a process for the epoxidation of olefins.

* * * * *